(12) United States Patent
Hogan et al.

(10) Patent No.: US 9,518,943 B2
(45) Date of Patent: Dec. 13, 2016

(54) TEMPERATURE MIMIC PROBE FOR FOOD PRODUCTS

(75) Inventors: Mark Hogan, Cardiff, CA (US); David Twining, Strawberry, CA (US)

(73) Assignee: LETTUCE BOX, LLC, Encinitas, CA (US)

( * ) Notice: Subject to any disclaimer, the term of this patent is extended or adjusted under 35 U.S.C. 154(b) by 415 days.

(21) Appl. No.: 14/233,187

(22) PCT Filed: Jun. 29, 2012

(86) PCT No.: PCT/US2012/044999
§ 371 (c)(1),
(2), (4) Date: Jan. 16, 2014

(87) PCT Pub. No.: WO2013/012546
PCT Pub. Date: Jan. 24, 2013

(65) Prior Publication Data
US 2015/0233847 A1    Aug. 20, 2015

Related U.S. Application Data

(60) Provisional application No. 61/509,029, filed on Jul. 18, 2011.

(51) Int. Cl.
*G01K 1/16* (2006.01)
*G01N 25/00* (2006.01)
(Continued)

(52) U.S. Cl.
CPC .................. *G01N 25/00* (2013.01); *G01K 1/08* (2013.01); *G01K 13/00* (2013.01); *Y10T 29/49826* (2015.01)

(58) Field of Classification Search
None
See application file for complete search history.

(56) References Cited

U.S. PATENT DOCUMENTS 4,577,475 A    3/1986   Herrera
5,282,554 A    2/1994   Thomas
(Continued)

FOREIGN PATENT DOCUMENTS

GB    2235780 A    3/1991
GB    2465019 A    5/2010

OTHER PUBLICATIONS

International Application No. PCT/US2012/044999, International Search Report and Written Opinion mailed Sep. 24, 2012 (10 pgs.).

*Primary Examiner* — Erica Lin
(74) *Attorney, Agent, or Firm* — Jonathan A. Kidney; TechLaw LLP

(57) ABSTRACT

A method and system for mimicking a thermal profile of a perishable product by fabricating a thermal mimicking probe (TMP). The TMP is obtained by forming a non-perishable, substantially solid material into a predetermined mass or shape, wherein the non-perishable material, in combination with the predetermined mass or size, has a temperature retention property similar to a perishable product; sealing an entirety of the formed material with a protective covering to form a core; accommodating a temperature sensor into a sensor side of the core; forming a first insulating layer on the sensor side of the core; and forming an enclosure of a second insulating layer that covers remaining sides of the core, wherein the first insulating layer is configured as a lid to the enclosure, wherein a change in temperature of a neighboring perishable product is substantially mimicked by readings from a temperature sensor in the core.

15 Claims, 11 Drawing Sheets

(51) Int. Cl.
 *G01K 13/00* (2006.01)
 *G01K 1/08* (2006.01)

(56) References Cited

U.S. PATENT DOCUMENTS 6,976,368 B1 12/2005 Lamstaes
2004/0159714 A1* 8/2004 Gatling .................. F25D 29/00
 236/51

* cited by examiner

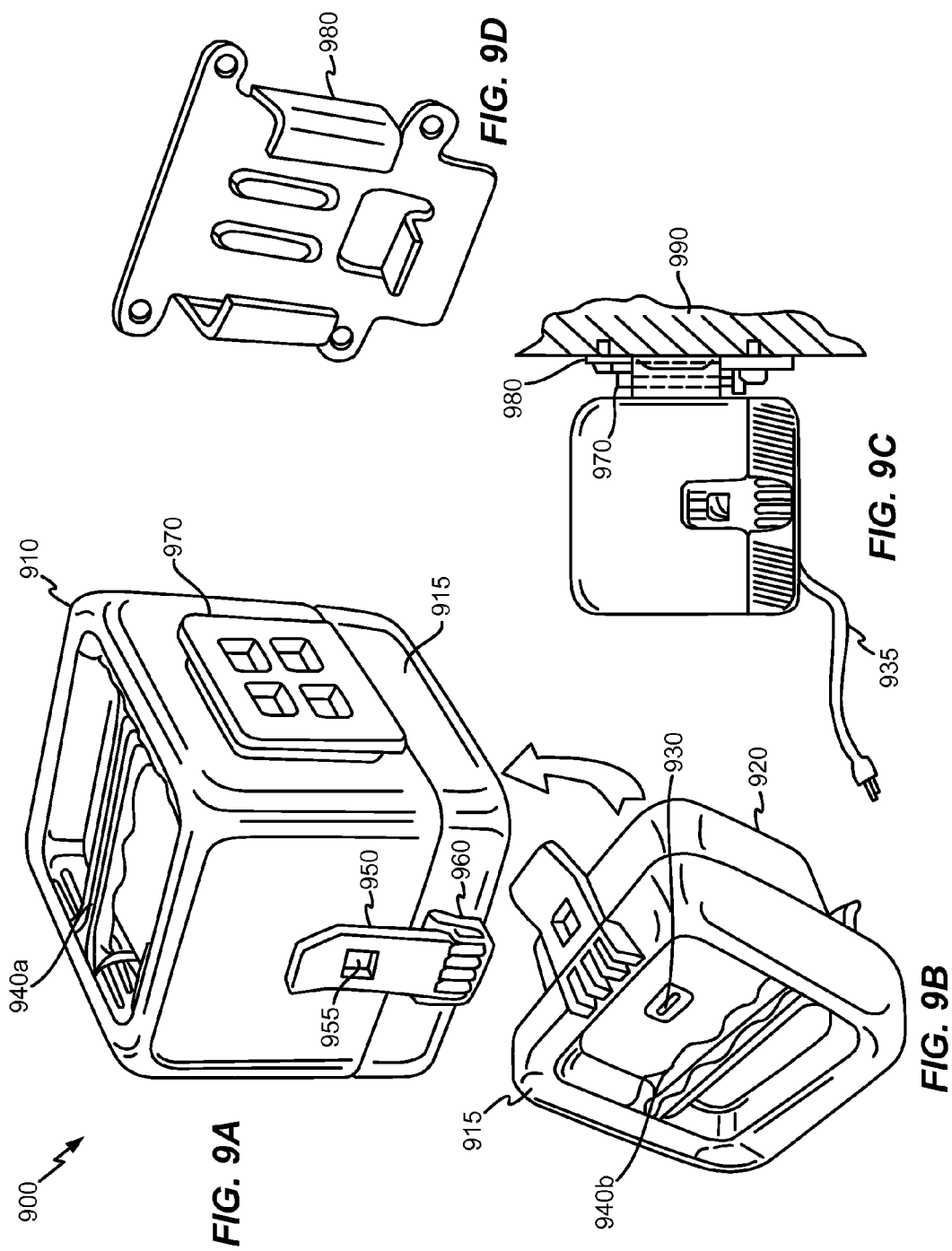

US 9,518,943 B2

TEMPERATURE MIMIC PROBE FOR FOOD PRODUCTS

CROSS-REFERENCE TO RELATED APPLICATION(S)

This application is a U.S. National Stage Filing under 35 U.S.C. 371 from International Patent Application Serial No. PCT/US2012/044999, filed Jun. 29, 2012, and published on Jan. 24, 2013 as WO 2013/012546 A1, which claims the benefit of priority U.S. Provisional Patent Application No. 61/509,029, filed Jul. 18, 2011, the contents of each of which are hereby incorporated by reference in their entireties.

BACKGROUND

Field

This invention relates to food temperature mimicry systems in the food storage and transportation industry. More particularly, it relates to a portable food emulator, suited for replicating a specific food product's temperature behavior.

Background

With increased health and liability concerns in the food services industry with respect to tainted or spoiled foods, and reductions in shelf life and quality, restaurants, grocery stores and food transporters have looked to sophisticated systems to monitor and control food products that are in cold storage. Typically, such systems involve tracking the temperature of the ambient air in the cold storage unit and sending an alarm if the temperature rises above an acceptable level. However, this approach does not accurately reflect the actual temperature inside the food product, the real medium that is of concern. In some companies, persons have been tasked to manually probe the product temperature (opening, probing, resealing), the performance of which, unfortunately, is known to be often falsified. Accordingly, erring on the side of caution, the food industry unnecessarily discards millions of dollars of suspect but un-spoiled food a year, putting a "tax" on the profitability of operations. Or, the food industry over-chills the products (thereby, spending millions on energy costs) to avoid concerns of spoilage.

Therefore, several attempts have been made in the industry to try to replicate a food proxy system for temperature monitoring, but the prior art all require certain compromises in transportability, durability and ease of operation, not to mention accuracy, expense of maintenance, etc. Accordingly, there has been a long-standing need in the food services industry for more effective solutions to these and other challenges in industry.

As detailed below, various system(s) and method(s) are presented that address the above concerns, thereby allowing more efficient monitoring of chilled or frozen food products' temperatures to provide significant energy and cost savings in the food industry.

SUMMARY

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

In one aspect of the disclosure, a method for mimicking a thermal profile of a perishable product by fabricating a thermal mimicking probe (TMP) is provided, comprising: forming a non-perishable, substantially solid material into a predetermined mass or shape, wherein the non-perishable material, in combination with the predetermined mass or size, has a temperature retention property similar to a perishable product; sealing an entirety of the formed material with a protective covering to form a core; accommodating a temperature sensor into a sensor side of the core; forming a first insulating layer on the sensor side of the core; and forming an enclosure of a second insulating layer that covers remaining sides of the core, wherein the first insulating layer is configured as a lid to the enclosure, wherein a change in temperature of a neighboring perishable product is substantially mimicked by readings from a temperature sensor in the core.

In other aspects of the disclosure, the above method is provided further comprising: placing the TMP in a container containing the perishable product, the container being a controlled temperature chamber and/or comprising chilling the core to the controlled temperature prior to placing it into the enclosure and/or wherein the first insulating layer contains a handle and is integrally attached to the core, and the insulating layers have an R value of approximately 6.4 R/inch and/or further comprising: attaching a mount to a side of the enclosure; and attaching the enclosure via the mount to a receiving bracket affixed to a surface of the controlled temperature chamber, wherein the mount enters the receiving bracket in an orientation substantially perpendicular to a side of the mount.

In another aspect of the disclosure, a thermal mimicking probe (TMP) device is provided, comprising: a non-perishable, substantially solid material formed into a predetermined mass or shape, wherein the non-perishable material, in combination with the predetermined mass or size, has a temperature retention property similar to a perishable product; a protective covering sealing an entirety of the formed material to form a core; a cavity in a sensor side of the core capable of housing a temperature sensor; a first insulating layer that covers a sensor-side of the core, having a data port on an exterior side of the first insulating layer; and an enclosure of a second insulating layer that covers remaining sides of the core, wherein the first insulating layer is configured as a lid to the enclosure, wherein a change in temperature of a neighboring perishable product is substantially mimicked by readings from a temperature sensor in the core.

In other aspects of the disclosure, the above method is provided, further comprising a temperature sensor in the temperature sensor cavity and/or further comprising a data cable connected to the data port, connecting the temperature sensor to an external logging device and/or wherein the non-perishable material is at least one of a plastic-based material, paraffin and beeswax and/or wherein the first and second insulating layers have an R value of approximately 9.6 $F*ft^2*hr/BTU$ and/or further comprising an integral handle disposed on an outer surface of at least the first and second insulating layers and/or wherein the perishable product is a food product and/or wherein the food product is at least one of chilled lettuce and frozen French fries and/or further comprising: a mount with defined sides attached to a side of the enclosure capable of enabling the enclosure to enter a receiving bracket in a substantially perpendicular orientation corresponding to a side of the mount and/or wherein the temperature sensor is removable and/or wherein the core is formed from at least one of plastic-based material with dimensions of approximately 8" L×6" W×6" H and beeswax with dimensions approximately 4" L×5" W×4" H, wherein the insulating layers are approximately 1-1.5 inches thick and/or further comprising a monitoring station coupled to the temperature sensor and/or further comprising a latch secured to at the first insulating layer and capable of coupling to the enclosure and/or further comprising a latch secured to at the enclosure and capable of coupling to the first insulating layer.

In another aspect of the disclosure, a method for fabricating a thermal mimicking probe (TMP) to mimic a thermal profile of a perishable product is provided, comprising: inserting a temperature probe into a container of a perishable product; measuring a first ambient temperature and first thermal response of the perishable product over a first period of time; forming a non-perishable, substantially solid material into a predetermined mass or shape, wherein the non-perishable material, in combination with the predetermined mass or size, has a thermal response profile similar to the perishable product; sealing an entirety of the formed material with a protective covering to form a core; placing a temperature sensor into a sensor side of the core; placing a first insulating layer on the sensor side of the core; forming an enclosure of a second insulating layer that covers remaining sides of the core, wherein the first insulating layer is configured as a lid to the enclosure, wherein the core, lid and enclosure form a TMP unit; measuring a thermal performance of the TMP unit as compared to a second ambient temperature and second thermal response of the perishable product over a second period of time, altering at least one of a size of the core and insulation thickness or R-factor; and utilizing an offset, if necessary, to bring the thermal performance of the TMP to substantially match one of the first and second thermal response of the perishable product.

BRIEF DESCRIPTION OF THE DRAWINGS

FIGS. 9A-D are illustrations of another exemplary TMP unit and associated hardware.

DETAILED DESCRIPTION

The Temperature Mimic Probe (TMP) for products can be composed of a critical mass of thermally responsive material, typically enclosed inside insulation which, in combination with standard temperature sensing device (such as, thermistor, thermocouple, thermometer, etc.), can be used to mimic the internal temperature of an actual box of food, for example, lettuce or other chilled (or frozen) food products. Non-limiting examples of such food products are French fries, chicken nuggets, orange juice, fresh chicken, fish, eggs, meat, and so forth—i.e., perishable food. The exemplary TMP described below was developed for lettuce mimicking, however, other foods or perishable goods can be mimicked, as desired.

Depending on the type of lettuce (whole, shredded, mixed, etc.) the size and shape of the TMP unit can be altered to more accurately track the type of food product. One or more temperature probes can be inserted into the TMP to gather the temperature of the TMP. The temperature probe(s) can be connected either by wire or wireless to an external temperature logger/monitor.

In addition to travel trailers, where temperature variations are known to be significant, the TMP can be used in static chillers (i.e., not in transportation), such as in restaurants and wholesale storage systems, distribution centers and so forth. When the unit is chilled to the same starting temperature as the actual box of lettuce or similar food product (for example, placed in the same storage unit as the food product) the temperature reading(s) within the TMP unit will approximate that of the actual food product as surrounding air temperature changes.

For rapid chilling, the core (TMP unit without surrounding insulation) of the exemplary TMP can placed into a cooler/chiller, allowing it to rapidly arrive at the ambient temperature, thus avoiding typical "chilling" delay times associated with prior art systems. This aspect provides significant time savings when implementing the TMP system into a new environment, as time-to-equilibrium delays at a loading station can be significantly reduced. Also, with respect to cost savings, only multiple cores need to be purchased, rather than prior art systems that require an integrated core and enclosure unit.

Prior to development of a prototype, warming and cooling samples were obtained using actual boxes of lettuce in a representative functional environment, and capturing temperature data before, during, and after each warming and cooling cycle. Using this empirical data, a foundation for thermal mimic development was attained. For example, the precise dimensions of the lettuce box, type of lettuce (e.g., iceberg vs. spring blend vs. etc.), the packing style (e.g., tightly packed vs. loosely packed vs. etc.), the lettuce processing (e.g., shredded, vs. whole leaf vs. etc.), and the location of the temperature probes within the box of tested product all affect the TMP.

Figure 1:
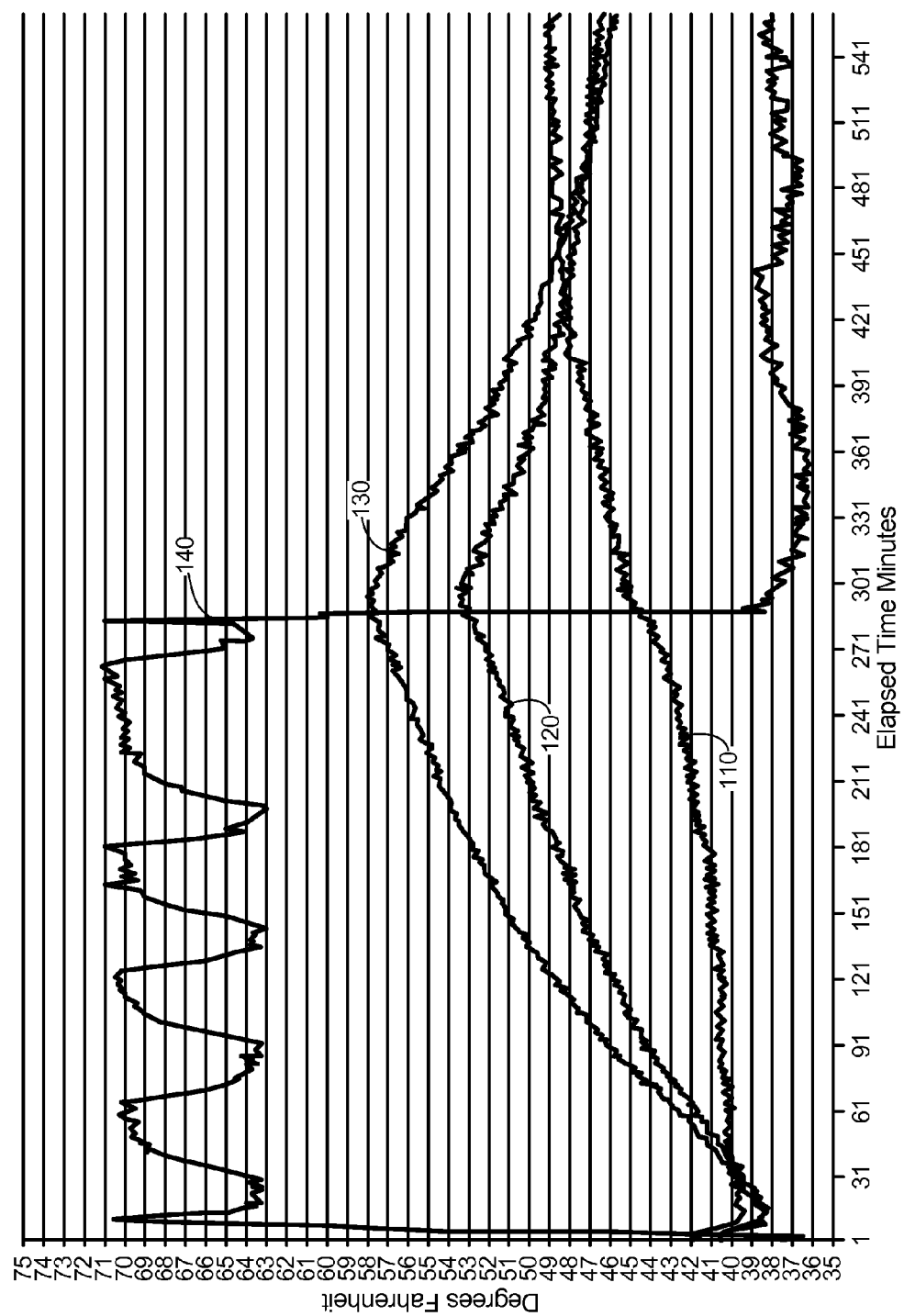
FIG. 1 is a plot of measured temperatures in a box of lettuce.

FIG. 1 is a plot of measured temperatures in a box of lettuce being warmed/cooled. Placing Type K thermocouples at various locations throughout a box of lettuce, temperatures T1 110, T1 120, and T3 130 were captured. The test box contained both bags of shredded iceberg lettuce and bags of whole leaf spring blend lettuce. The thermocouples were placed in 3 locations: between tightly packed bags of shredded iceberg lettuce (T1 110), between a bag of shredded iceberg lettuce and a bag of spring blend lettuce (T2 120), and between two bags of loosely packed spring blend lettuce (T3 130). A fourth thermocouple, T4 140, was placed outside nearby the test box of lettuce to monitor the ambient air temperature.

Cycling of the ambient temperature is performed in the first portion of the time line (0-300 minutes), whereas a sudden drop in ambient temperature is performed at the 300 minute interval. The temperature plots 110-130 demonstrate the temperature response for the respective location/bags of lettuce when exposed to ambient temperature 140. The same measurement process could be repeated for any variety of lettuce mixes, packing configurations, or box sizes, to yield different results. As well as for different types of foods/ perishable goods. It is noted here that while the exemplary embodiments are described in the context of perishable food products, the exemplary embodiments may also be applicable to non-food items, such as refrigerated medicines, chemicals, and so forth. Therefore, various modifications and changes may be made the design of the exemplary embodiments to make them suitable for other applications without departing from the spirit and scope of this disclosure.

Mathematical modeling was performed to formalize the empirical data into a predictable model: $T_L = T_{amb} - (T_{amb} - T_0)e^{t/\tau}$, where $T_L$ is the temperature of the food product at a given location, $T_{amb}$ is the ambient air temperature, $T_0$ is the initial temperature of the lettuce (which is assumed to be close to the initial temperature of the TMP) t is time and $\tau$ is the time constant. The time constant $\tau$ depends on the physical dimensions of the box of lettuce, the type of lettuce, the packing density, as well as thermal properties such as specific heat, mass density, thermal conductivity, and so forth. The thermal properties of lettuce, as well as other foods, are not well understood or well known, and published information is inconsistent at best, so experimental data can provide a solid baseline to replicate the actual temperature sensitivity of foods (noting that the packing of the food is a factor that may not be readily available).

By comparing the experimental data with the mathematical model, the time constants shown in Table 1 below were derived, corresponding to the various locations of the temperature monitoring as well as for the type of lettuce. Additionally, the corresponding average error values are included to indicate the accuracy of the model, when compared to actual data. The threshold for accuracy was placed at less that 2% in this instance, but can be adjusted as needed.

TABLE 1

| Location | Time constant $\tau$ | Error (average) |
| --- | --- | --- |
| T1 (shredded/shredded) | 2070.39 minutes | 1% |
| T2 (shredded/blend) | 382.70 minutes | 1% |
| T3 (blend/blend) | 254.78 minutes | 1% |

Understanding that a TMP for lettuce mimicking should be compact, lightweight, durable, material identification is of importance. Nearly any material could work if the dimensions were not important, but this would result in large and/or heavy TMP units. For example, a block of aluminum that accurately mimics the thermal properties of a box of lettuce would be many meters across and weigh thousands of pounds.

Consequently, the inventor reviewed thousands materials for their thermal properties, mass density, specific heat, thermal conductivity, etc., a balance between size, weight, availability, as well as material costs. One possible material was plastic-based, for example Poly(methylmethacrylate) (PMMA), which for whole lettuce, can be configured into a block of approximately 8 inches L, by 6 inches W, by 6 inches H, enclosed with R6 insulating material of approximately 1 inch thickness. The resulting lettuce plastic-based TMP unit was approximately 12 lbs in weight with total dimensions of 10 inches L by 8 inches W by 8 inches H and was built to mimic a shipping box of shredded lettuce having dimensions of approximately 17.5 inches L, by 10.5 inches W, by 8 inches H with a weight of approximately 20 lbs.

Another cost-effective material that came to light was wax (natural or paraffin) particularly beeswax, which offered most of the thermal properties sought. Some research suggests some inconsistency in the thermal properties of beeswax corresponding to the species of bee producing the wax (for example, "The Thermal Properties of Beeswaxes: Unexpected Findings," Buchwald, et al., Jan. 1, 2008, The Journal of Exploratory Biology, pgs. 121-127). However, Table 2 below details the thermal properties applied to our models, which proved to be accurate.

TABLE 2

| Property | Value | Units |
| --- | --- | --- |
| Specific Heat | 3.4 | kJ/kg * K |
| Mass Density | 0.961 | g/cm$^3$ |
| Thermal Conductivity | 0.15 | W/mK |
| Diffusivity | 0.05 | mm$^2$/s |

In preliminary models, a beeswax core encased in ⅛" acrylic was built, surrounded by foam lining of approximately 1.5 inch thickness, also encased in ⅛" acrylic. A thermocouple was inserted in the center of the beeswax core and testing was conducted by chilling the unit in a household refrigerator and then placing it in room temperature.

Figure 2:
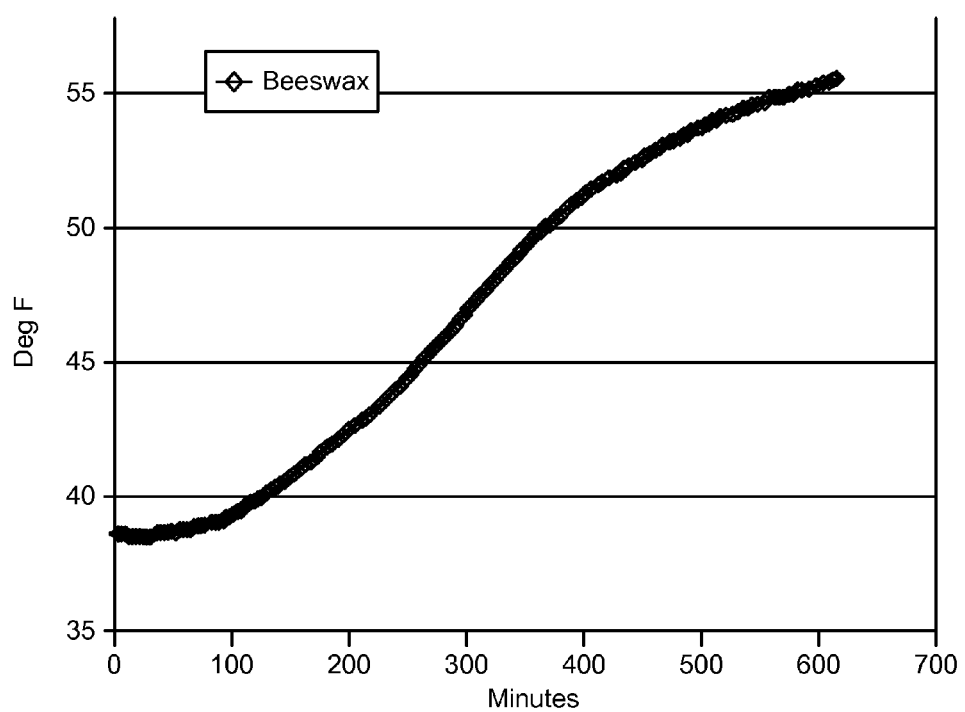
FIG. 2 is a plot of the thermal properties of beeswax.

FIG. 2 is a plot of the thermal behavior of a prototype beeswax core as a function of minutes (X-axis) and temperature (F degs for Y-axis), when removed from a refrigerator at approximately 38 F and placed into room temperature (approximately 60 F). Initial results showed that, as compared to the lettuce temperature samples of FIG. 1, some minor adjustments were necessary, specifically a larger core was implemented and thicker foam was utilized.

Specifically, in order to reduce overall thermal conductivity of the thermal mimic, a layer of material with very low thermal conductivity (therefore very high thermal resistivity) can be used. A closed cell polyisocranurate foam bonded to a durable non-glare (white matte) aluminum facer and reflective reinforced aluminum facer was utilized in some of the embodiments, understanding that other materials may be used, as according to design preference. Polyisocranurate foam of 1 inch thickness has the thermal properties listed in Table 3 below.

TABLE 3

| Property | Value | Units |
| --- | --- | --- |
| Specific Heat | 1.4 | kJ/kg * K |
| Mass Density | 0.032 | g/cm$^3$ |
| Thermal Conductivity | 0.024 | W/mK |
| Diffusivity | 0.54 | mm$^2$/s |

Of course, other materials that are within 20-40 percent of the above values may be used, depending on what core material is used, and relative size. For example, slightly different thermal properties of a 1.5 inch Thermasheath® polyisocranurate foam insulation are displayed in Table 4 below.

TABLE 4

| Property | Value | Units |
| --- | --- | --- |
| Specific Heat | 1.4 | kJ/kg * K |
| Mass Density | 0.032 | g/cm$^3$ |
| Thermal Conductivity | 0.0225 | W/mK |
| Diffusivity | 0.50 | mm$^2$/s |

Generally speaking, any insulation with a thermal resistance of generally 9.6 F*ft$^2$*hr/BTU was found to be effective, given the core material/sizes used. Of course, while 9.6 F*ft$^2$*hr/BTU was found to be effective for "lettuce," other thermal resistance rates may be used, depending on design preference.

In various embodiments a block of beeswax having dimensions of 4" L×5" W×4" H, with thermal properties described in Table 5 below, was used to form the core for the TMP.

TABLE 5

| Property | Value | Units |
|---|---|---|
| Specific Heat | 3.4 | kJ/kg * K |
| Mass Density | 0.961 | g/cm$^3$ |
| Thermal Conductivity | 0.15 | W/mK |
| Diffusivity | 0.05 | mm$^2$/s |

Understanding that beeswax was used since it demonstrated desirable thermal properties, any other material having a heat diffusivity of approximately the same amount (for example, 0.05 mm$^2$/s) can be used as a substitute. If the volume is increased slightly, then a material with slightly lower diffusivity could be utilized, the net effect being practically the same. If the volume is decreased slightly, conversely, a material with slightly lower diffusivity could be utilized. These adjustments are within the purview of one of ordinary skill in the art and as such, these and other modifications may be made without departing from the spirit and scope here. For example, in addition to a different core material, alternate geometric changes (cylinder, sphere, etc.) could also facilitated.

Using mathematical modeling and relevant materials, as identified above, a computer modeling approach was undertaken using finite element analysis. While not necessary, this approach provided rapid simulation of different possible sizes, shapes, ratios of materials, thicknesses, etc. to reduce the infinite possible combinations to a select few. While simulation software called LISA 7.6 was utilized, other possible modeling and analysis software such as SolidWorks® or COMSOL Multiphysics®, and so forth may be used, if so desired.

The results of the numerical analysis proved to be slightly different than that of the experimental data, therefore, minor adjustments to the TMP were made, such as increasing the size and including thicker foaming lining to more closely approximate the experimental data results. Of course, other changes could be implemented, but for this TMP model, these were the only changes implemented.

By combining the results from experimental measurements, numerical simulation, and fine-tuning/adjusting, various TMP models were fabricated that accurately mimicked the warming and cooling profile of lettuce in any size box, packing density, lettuce type, and so forth. For example, a TMP model can be quickly adjusted to mimic the temperature between two bags of densely packed shredded iceberg lettuce, or between two bags of loosely packed whole leaf spring blend lettuce, for example.

Of course, the above example was based on a TMP model designed for lettuce mimicking and therefore, a new TMP model can be developed to mimic other forms of food (or non-foods) that require temperature control, such as eggs, chicken, meats, vegetables, and so forth. Understanding that beeswax can operate as a suitable core material, other forms of wax, such as paraffin can be utilized, if so desired.

Figure 3A:
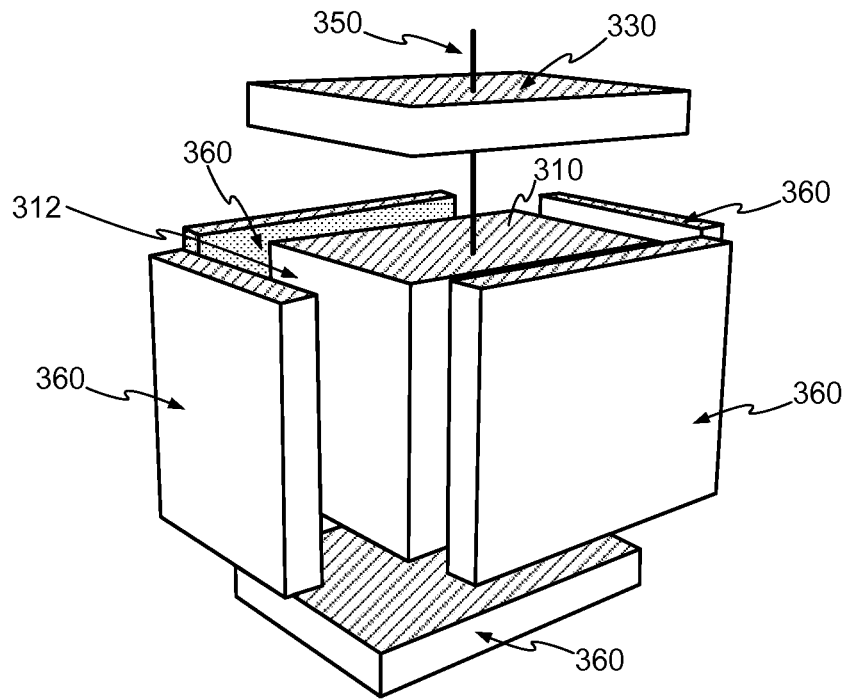
FIGS. 3A-B are illustrations of various exemplary temperature mimic probes (TMP).
Figure 3B:
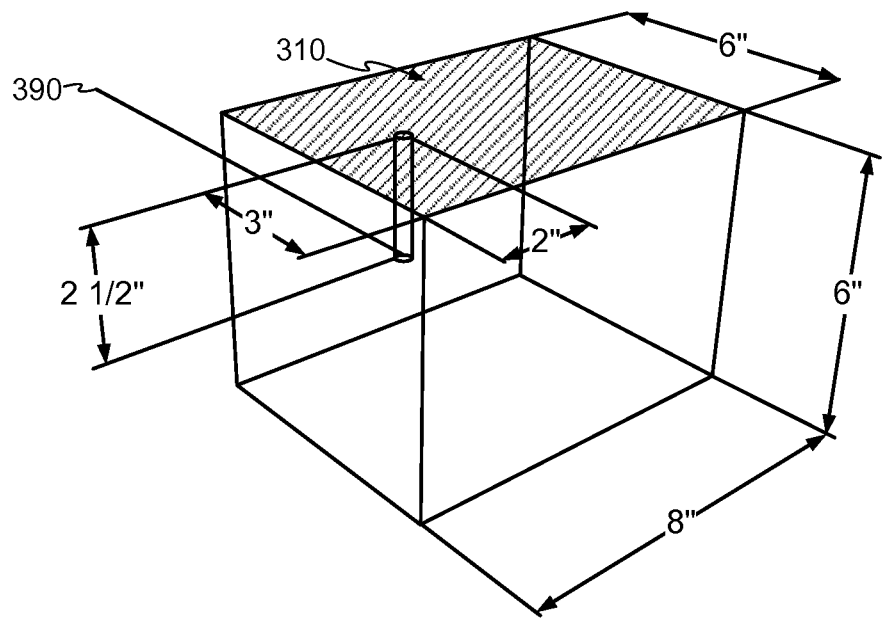

FIGS. 3A-B are illustrations of exemplary temperature mimic probes (TMP). FIG. 3A is a blow-up illustration showing the core 310 surrounded by insulation 360 and insulating lid 330. The core 310 is protected by a material 312 that "holds" the core material together as well as protects it from the environment. The material can be any moderately thermally transparent material, for example, plastic, or thin acrylic or Plexiglas®, and so forth. Thermal probe or sensor 350 protrudes through lid 330 into the core 310, having appropriate insertion holes.

FIG. 3B illustrates a specific thermal probe/sensor location of a core 310 composed from plastic with dimensions of 8" L×6"×6" H (1 inch R-6 insulation layer not show.) In this particular embodiment, the thermal probe/sensor is located "not" at the center of the core 310. However, centrally located probes can be used, if so desired. Point 390 represents the "bottom" of the hole accommodating the thermal probe/sensor.

Figure 4:
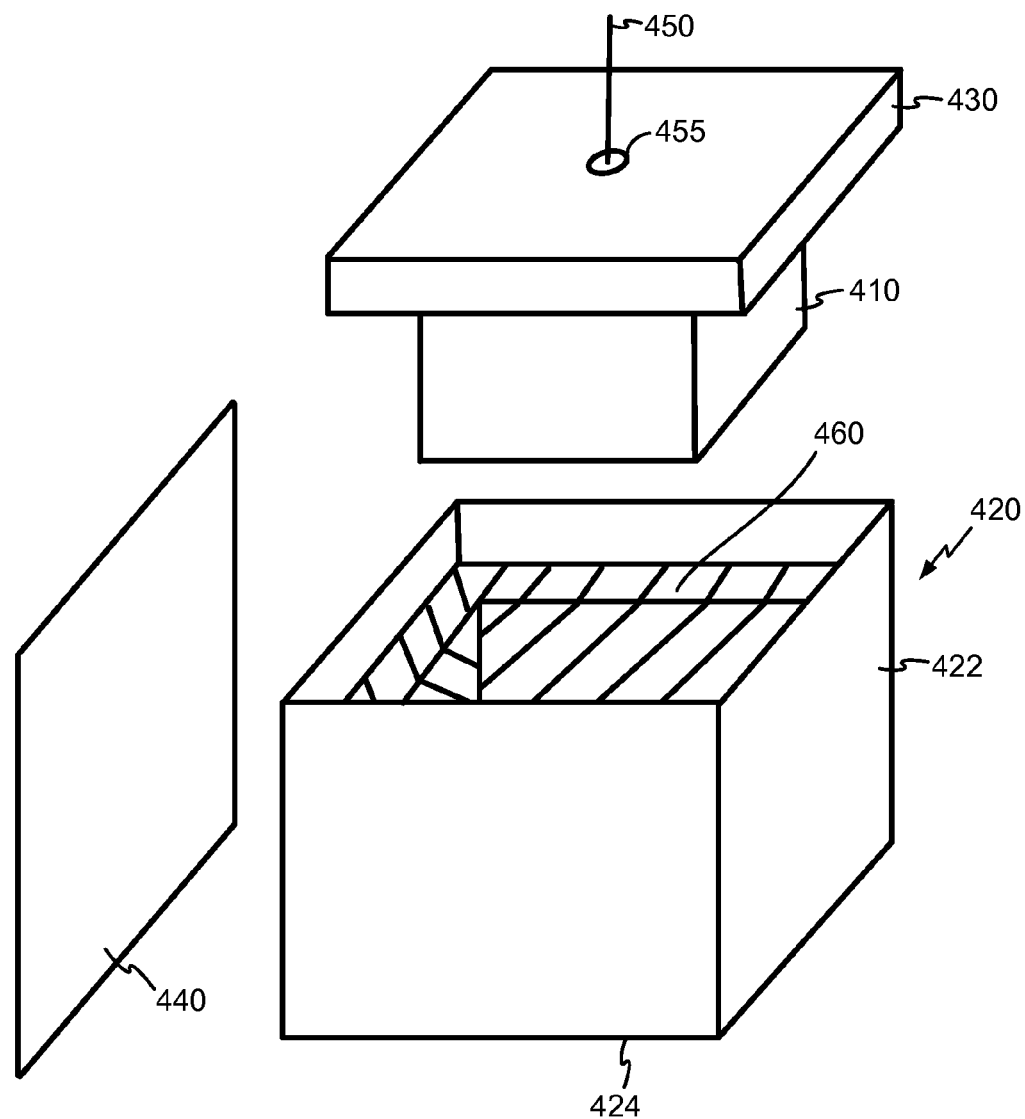
FIG. 4 is a blow-up illustration of another exemplary TMP.

FIG. 4 is a blow-up illustration of an exemplary TMP for lettuce mimicking. The exemplary TMP 400 comprises a core unit 410 encased by vessel 420 and lid 430. The vessel 420 can be attached to the wall (or bottom/top) of a supporting structure via a plate 440 that is bolted, glued, fastened, etc. to one of the sides (or bottom) of the vessel 420. A longitudinal temperature probe 450 is illustrated here as extending through lid 430 into core unit 410. Core unit 410 may be attached to lid 430 to allow the core unit 410 to be "lifted" via lid 430.

Sides 422 and bottom 424 of vessel 420 can be fabricated from acrylic or other impact resistant material, such as plastic. Similarly, top of lid 430 can be fabricated from an impact resistant material and/or plastic. The configuration shown here allows for the core unit 410 to be snugly inserted into cavity 460 of vessel 420. Insulating material(s) 460 such as Styrofoam® (or polyisocranurate foam, or polyisocranurate foam bonded to a durable non-glare facer and reflective facer) can be used to line the interior sides and bottom of vessel 420 and bottom of lid 430 to afford a complete insulating enclosure. Depending on the R-factor of the insulation, the insulating material(s) 460 can be approximately 1 to 2 inches thick. If the insulation is fragile, it may be covered by a plastic or other protective material.

In an exemplary embodiment, a sheet of Thermasheath®, approximately 1.5 inches thick was used, having an R value of approximately 9.6 F*ft$^2$*hr/Btu or equivalent to 6.4 R/inch. Of course, other materials may be used, depending on design preference. A retaining or sealing ring 455 may be placed over the temperature probe 450, to further seal the unit or to secure the temperature probe 450.

While the appearance of TMP 400 seems to be simple in nature, the benefits of having an "openable" enclosure as shown in FIG. 4 are numerous. For example, the core unit 410 can be rapidly tailored to mimic different food products. That is, core unit 410 can be switched out with another core unit (not shown) that is designed to replicate the temperature profile, for example, of tomatoes, or fresh meat, without having to replace the entire TMP 400. A simple removing of the temperature probe 450 and lifting of the lid 430 provides immediate access to the core unit 410, which may be interchanged, if so desired. This capability is very important when considering the time-sensitive scheduling of food deliveries. For example, in prior art systems, the mimicking device would need to be entirely replaced (i.e., unbolted from trailer wall) when swapping systems.

Further, when installing a replacement system in prior art systems, the mimicking system would have to be "chilled" to the equilibrium temperature prior to any tracking of the temperature. As there is a thermal "capacity" (or time constant) associated with the prior art mimicking system, a significant wait time is required to allow for the mimicking system to reach equilibrium temperature.

In contrast, the exemplary core unit 410 may be removed from the vessel 420 and exposed to the ambient air (i.e., chiller air) to allow it to chill more rapidly. With temperature probe 450 situated in the core unit 410 (presumably, but not necessarily without lid 430) the user can easily determine if core unit 410 has reached equilibrium temperature, whereupon the user can remove the temperature probe 450, insert the core unit 410 into vessel 420, put the lid 430 on the core unit 410 and insert temperature probe 450 into the lid 430 to seal the TMP 400. A significant reduction of wait time is achieved by the exemplary configuration. Alternatively, one of several core units 410 already set to equilibrium in a neighboring chiller could be brought in and inserted into vessel 420.

Temperature probe 450 can be easily replaced, being removable, in some embodiments, from the core unit 410 and lid 430. Some probes may become defective and rapid replacement can be facilitated by the user. It should be noted that not all embodiments are configured with a removable probe, as it may be desirable to have a probe that is fixed to lid 430 or even fixed to core 410. Therefore, the probe 450 may be permanently placed in the core unit 410 and operate via a wired or wireless mechanism. Temperature probe 450 may be wired to a remote logging/reporting system, either via direct wire connection or via wireless.

It should also be noted that while the embodiments of FIGS. 3-4 show lid 330, 430 separate from the core 310, 410, it is expressly understood that lid 330, 430 may be integrated to core 310, 410, to form a single unit. In this manner, the entire core (with lid) can be removed in one step.

While FIGS. 3-4 illustrate the exemplary TMP as having a box-like shape, it is expressly understood that other shapes and configurations can be used to accomplish the above-desired features. For simplicity sake, only a box-like enclosure was used, but rectangular, oval, circular, combinations of various volumes and shapes are contemplated and are understood to be within the spirit and scope of this disclosure.

Further, while the exemplary TMP is illustrated as having one longitudinal probe protruding into the top of the TMP, it is understood that the longitudinal probe (or other shaped probe) may be inserted at a non-top location, for example at a side of the TMP or at a bottom of the TMP. Thus, different entry points or locations (or number of probes) are contemplated as being within the spirit and scope of this disclosure.

Figure 5:
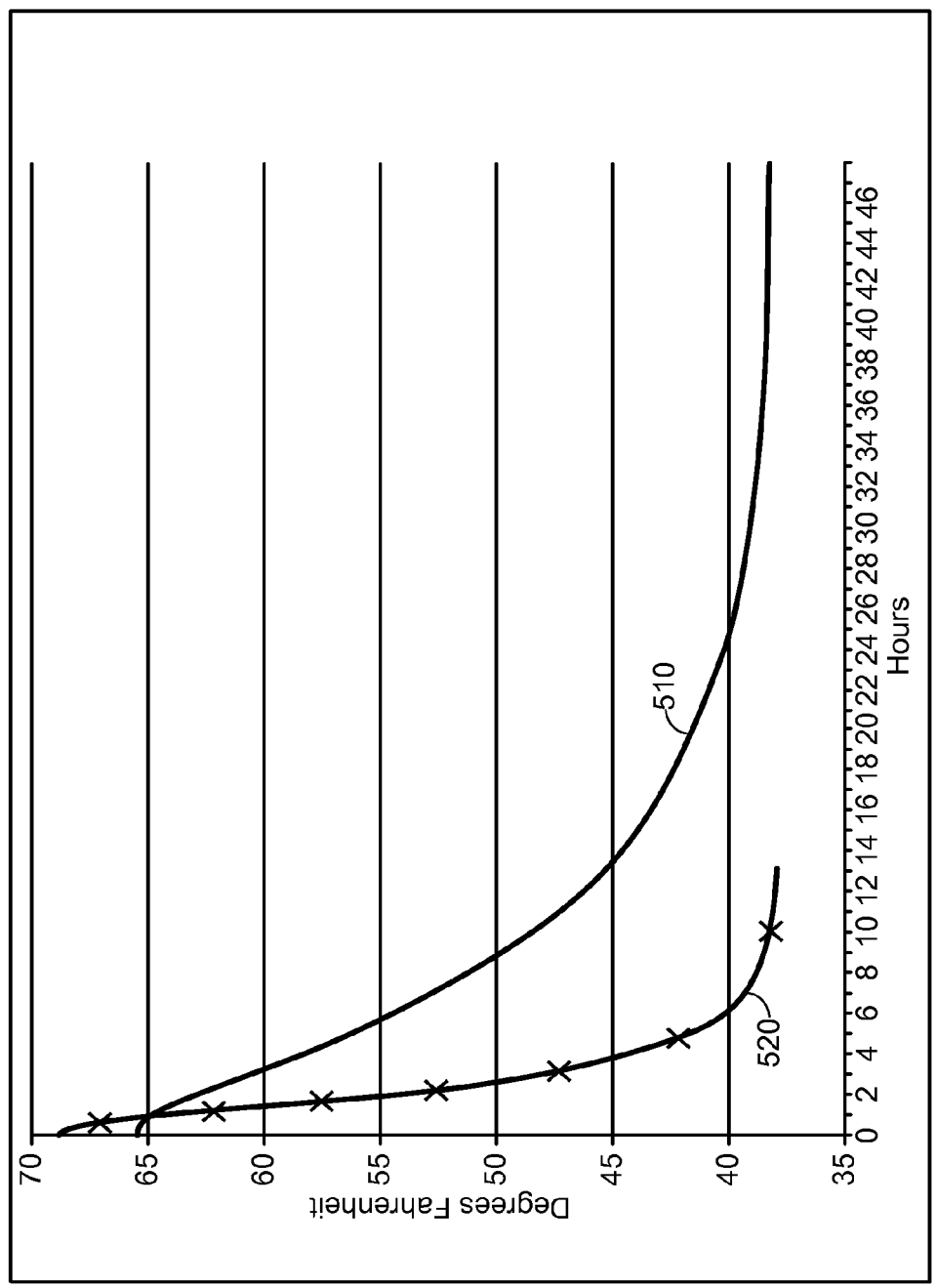
FIG. 5 is a temperature plot comparison of a non-removeable core versus removable core TMP unit.
Figure 6:
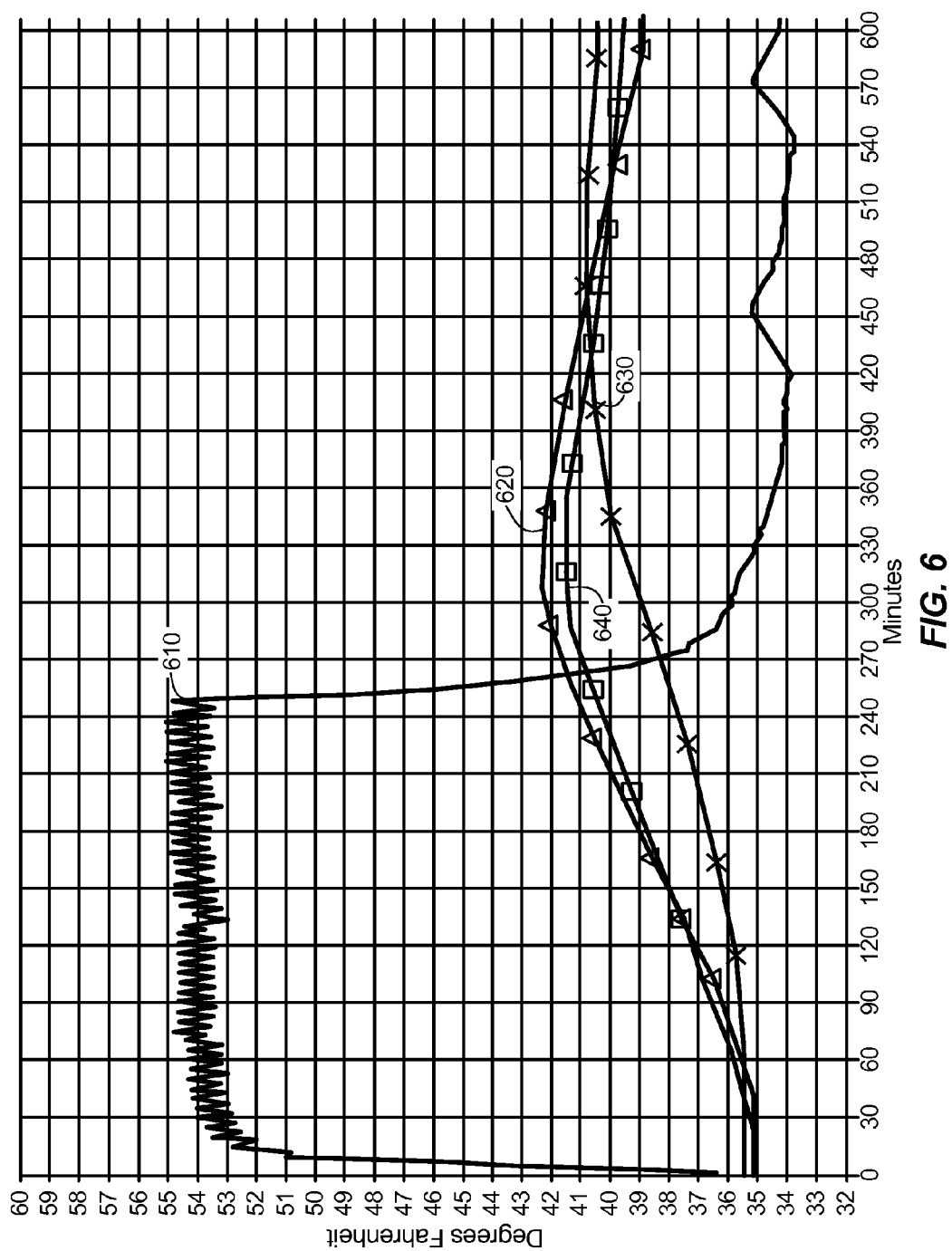
FIG. 6 is a temperature plot of an exemplary TMP as compared to chilled lettuce mix.

FIG. 5 is a temperature plot comparison of a system without a removeable core 510 and an exemplary TMP unit with a removable beeswax core 520, as the ambient temperature is raised to 65 F. It can be seen that the non-removable core 510 took over 36 hours to reach an equilibrium temperature of 38 F from 65 F, while an exemplary TMP unit (using a beeswax core) took less than 12 hours to reach the 36 F temperature. The significance of this is recognized when understanding that chillers for a refrigerated trailer will be turned off after the completion of a delivery, returning to the distribution center with an un-chilled trailer. While stored in this un-chilled trailer the mimic will rise in temperature response to the warming air in the trailer. Due to this warm the mimicking unit will require a "chill" time back to product equilibrium prior to re-deployment—a time which is significantly reduced with the exemplary TMP in comparison to prior art systems FIG. 6 is a plot of the temperature of an exemplary beeswax core TMP unit 620 as compared to ambient temperature 610, lettuce center temperature 630, and lettuce—one inch deep—temperature 640 in a cardboard box. The lettuce product was a McDonald's® salad blend, comprising: (a) 3×53 oz. shredded lettuce (vacuum packed and sealed) bags, and (b) 3×5 oz. spring mix (not vacuum packed and sealed) bags. The cardboard container box, when filled, weighted 10.75 lbs and was 11.5"×15.5"×9.25".

Three shredded lettuce bags were placed in the container box and a temperature probe was pierced through the top of the topmost bag and the tip of the probe was made to rest just below one leaf of lettuce from the top surface of the lettuce in the bag. This location is referred to as "one-inch deep" temperature location (aka 540). Three spring mix bags were placed over the shredded lettuce bags, to constitute the typical arrangement of lettuce bags in a lettuce container box.

The "center" temperature location 630 is obtained by piercing the topmost shredded lettuce bag, but from the bottom of the bag with the probe made to rest in the center of the lettuce in the bag. Three spring mix bags were placed over the shredded lettuce bags to constitute the typical arrangement of lettuce bags in a lettuce container box. The box was closed and resealed and measurements were taken.

As can be seen in FIG. 6, as ambient temperature 620 is dropped from 34-36 F (cycling is evident in the chiller) at around the 250 minute marker, the temperature 620 of an exemplary TMP closely tracks the temperature of "one-inch" 640. The "center" temperature 630, understandably (having more mass around the center) changes its temperature more slowly than "one-inch" temperature 640.

Figure 7:
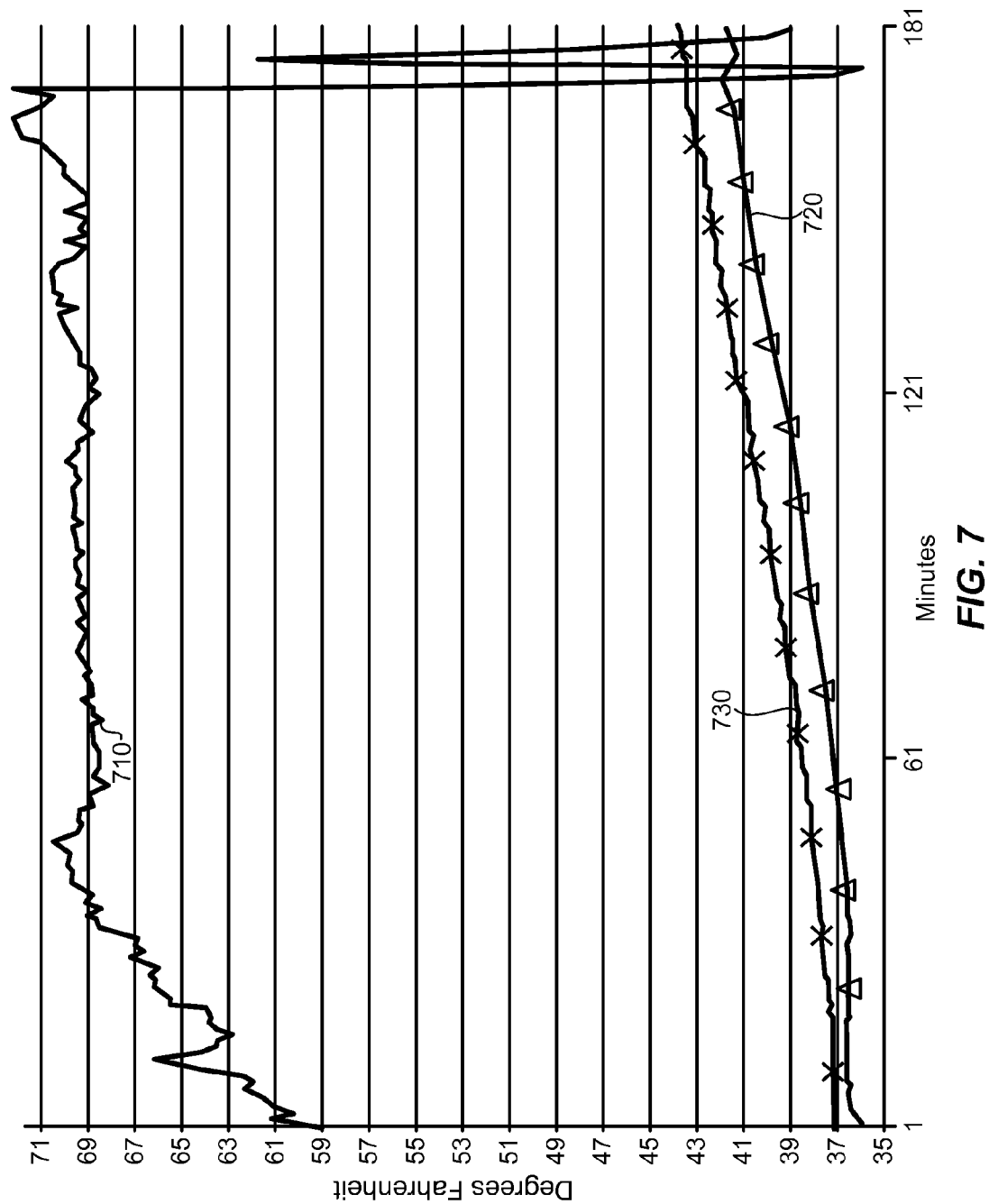
FIG. 7 is a temperature plot of an exemplary TMP as compared to chilled shredded lettuce.

FIG. 7 is another plot of temperature comparisons, using a cardboard container box entirely filled with shredded lettuce. The box was 17.5" L×8" W×10.5" H and contained four bags of 1.25 lbs and six bags of 2.5 lbs shredded iceberg lettuce. The temperature probe was placed under the center of the topmost 1.25 lbs bag, being sandwiched by another 1.25 lbs bag. This position constituted a distance of approximately 1.5" from the top of the sealed container box and is represented by plot line 720, whereas the exemplary TMP temperature is represented by plot line 730, with ambient temperature represented by plot line 710.

As can be seen in this FIG. 7, the ambient temperature 710 is gradually raised from 59 F to 70 F over a period of approximately 180 minutes. The 1.5" lettuce temperature 720 and the exemplary TMP temperature 730 are seen to track very closely to each other, differing perhaps by one degree or more. While the temperatures are not exact, an offset can be used to correct the TMP results to match the lettuce temperatures.

This test utilized an exemplary TMP with a beeswax core having dimensions of 4" L×5" W×4" H surrounded by insulation having an R-Value of 9.6 $F*ft^2*hr/Btu$. The temp sensor is placed center of the core.

Figure 8:
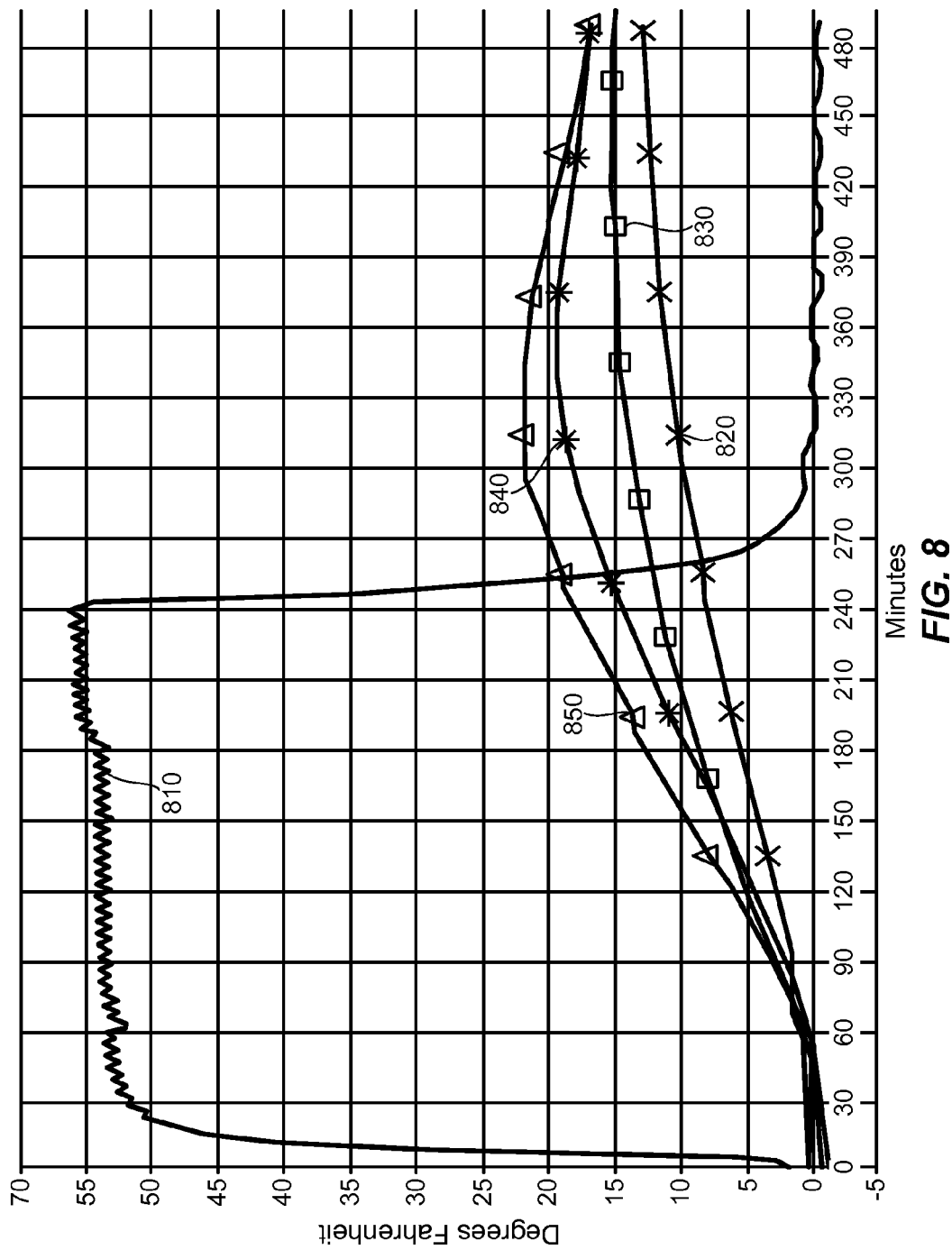
FIG. 8 is a temperature plot of exemplary TMPs as compared to frozen French fries.

FIG. 8 is a plot showing the temperature response for exemplary lettuce-designed TMPs to a box of chilled French fries. The cardboard box has dimensions of 16" L×13" W×13" H and contained eight bags of frozen French fries, the total weight being 36 lbs. The plot shows ambient temperature 810 being raised to about 55 F and then dropped to OF in the 240-270 minute time frame. Two versions of the lettuce-designed TMP were tested, one standard sized unit having 80 cubic inches of volume and one having 1.5 times the standard volume (i.e., 120 cubic inches).

Temperature probes were placed at the center 820 of the box and one bag deep 830 from the side of the box (centered, but approximately 2.6" inches from the side wall). Food Temperature Mimic Probe (FTMP) #1 represents the standard unit temperature 850 and FTMP #2 represents the larger unit temperature 840. The plot shows similar behavioral profiles for FTMP #1 (850) and FTMP #2 (840), recognizing that an offset(s) can be calibrated into the FTMPs to more closely track the French fry temperatures 820, 830. Recognizing that French fries stored at the 55 F temperature shown in FIG. 8 typically is not the norm (French fries thawing out at temperatures above 32 F) but at lower temperatures, it is anticipated that the exemplary FTMPs will perform more accurately within these smaller temperature swings.

Notwithstanding the above, plot demonstrates FTMP #2 850 to exhibit a temperature tracking profile that is between the center and one-bag deep locations 820 and 830, respectively. Thus, a lettuce-designed TMP can be simply modified (in this case, increased in volume by 50%—aka, FTMP #2) to closely track the temperature behavior of frozen French fries. Therefore, by one or more simple modifications, the exemplary TMP can be altered to mimic non-lettuce food products. Other alternations such as increasing or decreasing the insulating layer may be utilized to allow for more rapid or slower responses.

Accordingly, it is understood that the exemplary TMP can be easily configured to track other forms of chilled/frozen foods or perishable products by sampling a representative set of temperature responses and simply adjusting the exemplary TMP's basic features (size, insulation, etc.) to arrive at a reasonable mimicking TMP.

FIGS. 9A-D are illustrations of another exemplary TMP unit and associated hardware. FIG. 9A illustrates a TMP unit 900 in an inverted position with base 910 and integrated handle 940*a*, allowing easy grasping of the base 910. The integrated handle 940*a* is shown a being housed in a cavity in the top of the base 910, allowing the handle 940*a* to be easily grasped and also preventing the handle 940*a* from being externally exposed (and subject to damage from striking an object). A locking or latching mechanism 950 is coupled to lid 915 of the inverted TMP that "latches" the lid 915 via tab 955 to base 910 of the TMP, allowing easy detachment of the lid 915 from the base 910. While a clamping latch 950 is shown in FIG. 9A, other types of latches or securing mechanisms may be used, according to design preference. FIG. 9A also shows a side bracket 970 that allows the TMP unit 900 to be easily attached to a side wall of a chiller/truck/etc.

FIG. 9B illustrates the detached lid 915 of the TMP, with accompanying integrated handle 940*b* and temperature probe connection 930. This embodiment illustrates the temperature probe to be embedded in the core 920, having a connection point 930 located at the "surface" of the TMP. However, it is understood that the temperature probe connection 930 may be located at any position, side or section of the TMP, without departing from the spirit and scope herein. FIG. 9B also illustrates lid 915 as being "integrated" to the core 920, forming a single lid/base and core unit. That is, core 920 is directly attached to lid 910. Of course, in some embodiments, instead of the lid 915, it may be desirable to have the core 920 attached to the base 910, with accompanying temperature probe connection 930 disposed therein. Accordingly, depending on implementation objectives, the core 920 may be attached/integral to either the lid 915 or base 915.

While these embodiments contemplate the temperature probe (not shown) to be embedded in the core 920, in some embodiments, the temperature probe may be removable, via temperature probe connection 930—that is, the temperature probe may be designed to be integral with temperature probe connection 930, so that removing temperature probe connection 930 operates to remove the temperature probe.

FIGS. 9C-D illustrate an exemplary TMP attached to a wall 990 of a chiller unit, via bracket 970 and mating bracket 980, allowing easy removal and attachment of the exemplary TMP to a chiller or storage surface. Bracket 970 is shown as being substantially "square" resulting in the TMP being able to be mounted in any of four ways—corresponding to the sides of the square. This is significant, as the temperature probe connection 930 on the TMP can then be made to face in any of multiple directions (up, down, left, right.) In this way the temperature probe connection 930 can be positioned in the most convenient manner possible for connection to the data logger, thermometer unit by the person deploying the unit. In other embodiments, the bracket 970 may have more than four sides (e.g., six, eight, etc.) to allow easy entry into mating bracket 980, as well as allow different angels of attachment. Brackets/mating brackets, attachment means, mechanisms are well known in the art and therefore, further explanation is not provided. However, it is expressly understood that other forms of attachment, both for the base 910, lid 915, bracket 970 and mating bracket 980 are contemplated to be within the purview of one of ordinary skill in the art, and accordingly may be used herein. For example, bracket 970 and mating bracket 980 may be reversed, if so desired, or a clamping, latching, screwing, etc. mechanism may be utilized.

The wall 990 may be a floor, ceiling, side wall or other surface in the storage structure. The Temperature probe line 935 is illustrated as being coupled to the TMP via a bottom temperature probe connection 930 (not seen). As noted above, Temperature probe line 935 may be coupled to the TMP via a connection at other locations on the TMP.

Figure 10A:
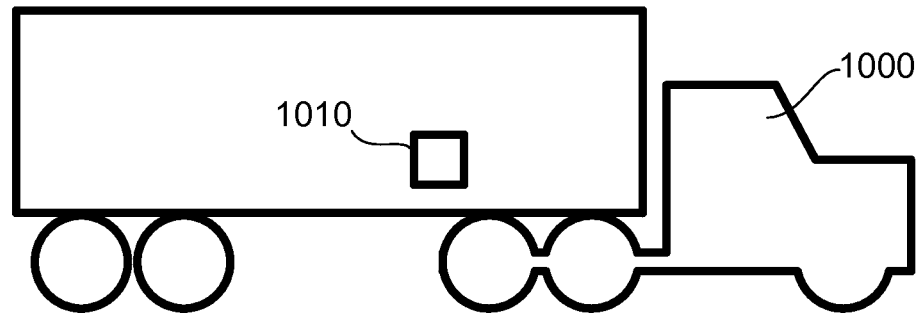
FIGS. 10A-B are illustrations of typical deployment scenarios for an exemplary TMP.
Figure 10B:
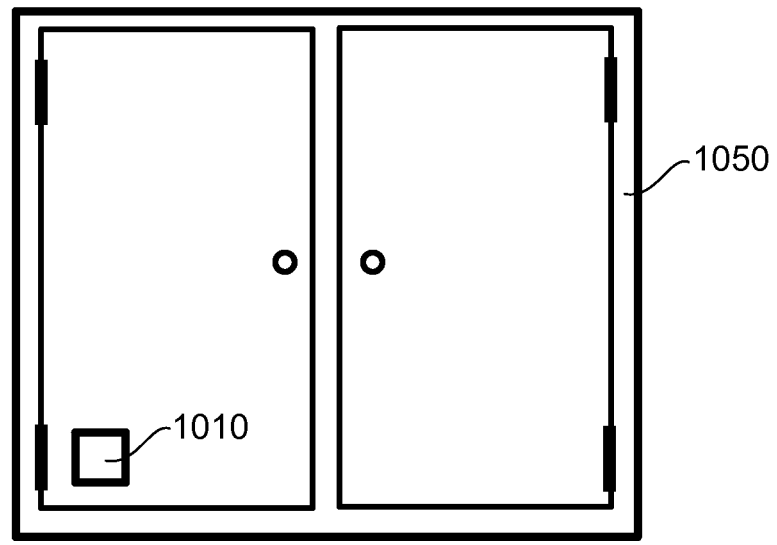

FIGS. 10A-B are illustrations of typical deployment scenarios for an exemplary TMP. FIG. 10A illustrates an exemplary TMP unit 1010 in the trailer of a truck 1000 and is understood to be self-explanatory. FIG. 10B illustrates an exemplary TMP unit 1010 in a cold storage chiller 1050 and is also understood to be self-explanatory. It is presumed, though not necessary, in operation, the TMP unit 1010 is connected to an external temperature monitoring system or data logger (not shown). While FIGS. 10A-B show two possible deployment scenarios, other possible deployment scenarios are contemplated, such as multiple units in a large distribution center, or deployed with a "pallet" of goods (this allows each pallet to be individually monitored), and so forth. Accordingly, other scenarios are contemplated as being within the spirit and scope of this disclosure.

Figure 11A:
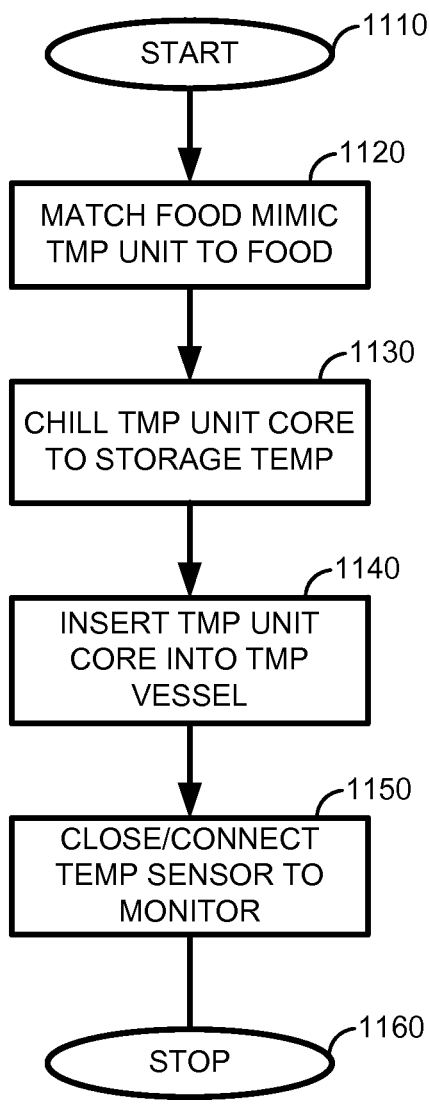
FIGS. 11A-B are process flow diagrams showing possible implementation steps for an exemplary TMP.
Figure 11B:
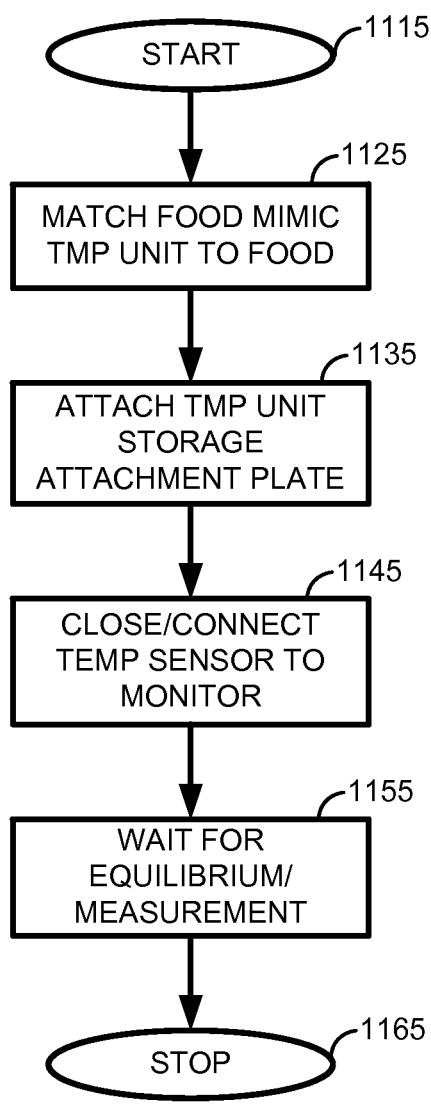

FIGS. 11A-B are process flow diagrams showing possible implementation steps for an exemplary TMP. FIG. 11A's process begins 1110 with matching 1120 a TMP unit to the food type/arrangement being monitored. The core of the TMP unit is next chilled 1130 to the storage room/trailer's temperature. Next, the chilled core is inserted 1140 into the TMP vessel that is situated in the storage room/trailer/etc. The TMP unit is "closed" and the temperature sensor is inserted and connected to a monitoring station 1150. The process stops 1160.

FIG. 11B's process begins 1115 with matching 1125 a TMP unit to the food type/arrangement being monitored. The TMP unit is "attached" 1135 to the storage room/trailer/etc. wall or floor or ceiling. The TMP unit is "closed" and the temperature sensor is inserted and connected to a monitoring station 1145. The TMP unit is measured to determine if it has reached the designated equilibrium temperature 1155. The process stops 1165.

Based on the above description, an exemplary TMP (and variations thereof) have been developed that accurately mimic the thermal properties of lettuce and French fries. Additionally, while the exemplary TMP was developed using lettuce/French fries as the tested food product(s), it is understood that other food products may have very similar thermal properties (recognizing that most foods are substantially water infused) by utilizing the described steps of measuring a sample product, comparing measurements to a tested TMP unit, and altering characteristics (such as core material, size, and insulation) of the TMP unit to match the sample product.

Further, in addition to developing an TMP that accurately tracks a food product's thermal properties, the exemplary TMP design is such that it is highly portable, easy to replace and easy to attain equilibrium temperature. These non-food related properties are particularly relevant to the food transportation industry where time spent waiting for a TMP to arrive at equilibrium, replacement time, etc. bears significant costs to the transporter. Therefore, the combination of an accurate TMP and an easily maintainable, quick to use TMP is highly sought after in the food transportation industry. In fact, a major food distributor/retailer has recognized these advantages and the exemplary TMP is currently being tested for nationwide and worldwide deployment.

Again, it should be understood that the applicability of the exemplary TMP(s) described herein are not limited to tested foods, but can be readily adapted without undue experimentation to arrive at servicing other food products, such as milk, eggs, vegetables, fruit, meat, frozen foods, etc. Moreover, it is contemplated that the exemplary TMP(s) can be utilized for mimicking perishable goods such as pharmaceuticals, chemicals, and other non-food related materials.

It will be understood that many additional changes in the details, materials, steps and arrangement of parts, which have been herein described and illustrated to explain the nature of the invention, may be made by those skilled in the art within the principle and scope of the invention as expressed in the appended claims.

What is claimed is:

1. A method for fabricating a rapid chillable thermal mimicking probe (TMP) for use with perishable products, comprising:
    forming a non-perishable, substantially solid material into a predetermined mass or shape, wherein the non-perishable material, in combination with the predetermined mass or size, has a temperature retention property similar to a perishable product;
    sealing an entirety of the formed material with a protective covering to form a core;
    accommodating a temperature sensor into a sensor side of the core;
    forming a first insulating layer on the sensor side of the core;
    forming the core, temperature sensor and a first insulating layer into a single integrated core assembly, configured as a removable lid;
    forming a carrying handle to the integrated core assembly;
    forming a second insulating layer that covers remaining sides of the core assembly, wherein when mated with the second insulating layer forms a TMP; and
    forming external latches on the TMP extending from either the core assembly or second insulating layer across to the opposite second insulating layer or core assembly, to secure together the core assembly and second insulating layer, wherein the latches provide easy detachment of the core assembly from the second insulating layer, wherein the core assembly can be quickly chilled via easy removal from the second insulating layer and placement into a chiller,
    wherein a change in temperature of a perishable product is substantially mimicked by readings from the temperature sensor in the core of the TMP.

2. The method of claim 1, wherein the insulating layers have an R value of approximately 6.4 R/inch.

3. The method of claim 1, further comprising:
    attaching a mount to a side of the TMP, the mount enabling the TMP to be attached to a receiving bracket in a
    controlled temperature chamber.

4. A rapid chillable thermal mimicking probe (TMP) device for mimicking a perishable product, comprising:
    a non-perishable, substantially solid material formed into a predetermined mass or shape, wherein the non-perishable material, in combination with the predetermined mass or size, has a temperature retention property similar to a perishable product;
    a protective covering sealing an entirety of the formed material to form a core;
    a cavity in a sensor side of the core capable of housing a temperature sensor;
    a first insulating layer that covers a sensor-side of the core, having a data port on an exterior side of the first insulating layer, wherein the first insulating layer and core form an integrated core assembly, configured as a removable lid;
    a carrying handle attached to the core assembly;
    an enclosure of a second insulating layer that covers remaining sides of the core assembly, wherein when mated with the core assembly, forms a TMP; and
    external latches on the TMP extending from either the core assembly or second insulating layer across to the opposite second insulating layer or core assembly, to secure together the core assembly and second insulating layer, wherein the latches provide easy detachment of the core assembly from the second insulating layer, wherein the core assembly can be quickly chilled via easy removal from the second insulating layer and placement into a chiller, and
    wherein a change in temperature of a perishable product is substantially mimicked by temperature sensor readings.

5. The device of claim 4, further comprising a temperature sensor in the temperature sensor cavity.

6. The device of claim 5, further comprising a data cable connected to the data port, connecting the temperature sensor to an external logging device.

7. The device of claim 4, wherein the non-perishable material is at least one of a plastic-based material, paraffin and beeswax.

8. The device of claim 4, wherein the first and second insulating layers have an R value of approximately 9.6 $F*ft^2*hr/BTU$.

9. The device of 4, wherein the perishable product is a food product.

10. The device of claim 9, wherein the food product is at least one of chilled lettuce and frozen French fries.

11. The device of claim 4, further comprising:
    a mount with defined sides attached to a side of the TMP enabling the TMP to to be attached to a receiving bracket in a substantially perpendicular orientation corresponding to a side of the mount.

12. The device of claim 5, wherein the temperature sensor is removable.

13. The device of claim 4, wherein the core is formed from at least one of a plastic-based material with dimensions of approximately 8" L×6" W×6" H and beeswax with dimensions approximately 4" L×5" W×4" H, wherein the insulating layers are approximately 1-1.5 inches thick.

14. The device of claim 5, further comprising a monitoring station coupled to the temperature sensor.

15. A method for fabricating a thermal mimicking probe (TMP) to mimic a thermal profile of a perishable product, comprising:
- inserting a temperature probe into a container of a perishable product;
- measuring a first ambient temperature and first thermal response of the perishable product over a first period of time;
- forming a non-perishable, substantially solid material into a predetermined mass or shape, wherein the non-perishable material, in combination with the predetermined mass or size, has a thermal response profile similar to the perishable product;
- sealing an entirety of the formed material with a protective covering to form a core;
- placing a temperature sensor into a sensor side of the core;
- placing a first insulating layer on the sensor side of the core, the first insulating layer and core forming an integrated core assembly, configured as a removable lid;
- forming a carrying handle on the core assembly;
- forming an enclosure of a second insulating layer that covers remaining sides of the core assembly, wherein the core assembly and enclosure of the second insulating layer, when joined together form a TMP unit;
- external latches spanning the core assembly and the enclosure of the second insulating layer, securing the core assembly and the enclosure of the second insulating layer together, wherein the latches provide easy detachment of the core assembly from the enclosure of the second insulating layer so the core assembly can be quickly chilled via easy removal from the second insulating layer and placement into a chiller;
- measuring a thermal performance of the TMP unit as compared to a second ambient temperature and second thermal response of the perishable product over a second period of time,
- altering at least one of a size of the core and insulation thickness or R-factor; and
- utilizing an offset, if necessary, to bring the thermal performance of the TMP unit to substantially match one of the first and second thermal response of the perishable product.

* * * * *